United States Patent
Walulik et al.

(10) Patent No.: US 7,449,023 B2
(45) Date of Patent: Nov. 11, 2008

(54) METHOD AND APPARATUS FOR THE EXTERNAL FIXATION AND CORRECTION OF BONE

(75) Inventors: Stephen B. Walulik, Blairstown, NJ (US); Kirk J. Bailey, Blairstown, NJ (US); Takkwong Ross Leung, Piscataway, NJ (US); Richard Davidson, Haveford, PA (US)

(73) Assignee: EBI, LLC, Parsippany, NJ (US)

( * ) Notice: Subject to any disclaimer, the term of this patent is extended or adjusted under 35 U.S.C. 154(b) by 511 days.

(21) Appl. No.: 10/619,536

(22) Filed: Jul. 15, 2003

(65) Prior Publication Data

US 2005/0113829 A1  May 26, 2005

Related U.S. Application Data

(60) Provisional application No. 60/395,814, filed on Jul. 15, 2002.

(51) Int. Cl.
*A61B 17/00* (2006.01)
*A61F 4/00* (2006.01)
*A61F 5/04* (2006.01)

(52) U.S. Cl. ........................................................ 606/59
(58) Field of Classification Search ............. 606/53–59; 403/53, 105
See application file for complete search history.

(56) References Cited

U.S. PATENT DOCUMENTS

| | | |
|---|---|---|
| 4,006,740 A | 2/1977 | Volkov et al. |
| 4,488,542 A | 12/1984 | Helland |
| 4,624,249 A | 11/1986 | Alvarez Cambras |
| 4,628,922 A | 12/1986 | Dewar |
| 4,782,842 A | 11/1988 | Fietti, Jr. |
| 5,062,844 A | 11/1991 | Jamison et al. |
| 5,100,403 A | 3/1992 | Hotchkiss et al. |
| 5,102,411 A | 4/1992 | Hotchkiss et al. |
| 5,372,597 A | 12/1994 | Hotchkiss et al. |
| 5,376,091 A * | 12/1994 | Hotchkiss et al. ............ 606/55 |
| 5,496,319 A | 3/1996 | Allard et al. |
| 5,681,309 A | 10/1997 | Ross, Jr. et al. |
| 5,700,263 A | 12/1997 | Schendel |
| 5,702,389 A | 12/1997 | Taylor et al. |
| 5,846,245 A | 12/1998 | McCarthy et al. |
| 5,863,292 A | 1/1999 | Tosic |
| 5,885,282 A | 3/1999 | Szabo |
| 5,971,984 A | 10/1999 | Taylor et al. |

(Continued)

FOREIGN PATENT DOCUMENTS

DE  3802743  * 3/1989

*Primary Examiner*—Anu Ramana
(74) *Attorney, Agent, or Firm*—Harness, Dickey & Pierce, P.L.C.

(57) ABSTRACT

An external fixation device includes a frame assembly having a first arc segment and a second arc segment. The first arc segment is for interconnection to a first bone portion. The second arc segment is for interconnection to a second bone portion. The first arc segment is coupled to the second arc segment for relative rotation. The external fixation assembly additionally includes an articulating module. The articulating module includes a central member, a first pivot segment and a second pivot segment. The first pivot segment is coupled to the central member for driven rotation about a first pivot axis. The second pivot segment is coupled to the central member for driven rotation about a second pivot axis. The second pivot axis is substantially perpendicular to the first pivot axis.

6 Claims, 11 Drawing Sheets

U.S. PATENT DOCUMENTS

| | | |
|---|---|---|
| 5,997,537 A | 12/1999 | Walulik |
| 6,019,769 A * | 2/2000 | McCarthy et al. ............ 606/105 |
| 6,113,599 A * | 9/2000 | Landsberger ................. 606/60 |
| 6,129,727 A | 10/2000 | Austin et al. |
| 6,355,037 B1 | 3/2002 | Crosslin et al. |
| 6,860,883 B2 | 3/2005 | Janowski et al. |
| 2004/0116926 A1 * | 6/2004 | Venturini et al. .............. 606/56 |

* cited by examiner

METHOD AND APPARATUS FOR THE EXTERNAL FIXATION AND CORRECTION OF BONE

CROSS-REFERENCE TO RELATED APPLICATION

This application claims priority to a provisional patent application which has been assigned U.S. Ser. No. 60/395,814, filed Jul. 15, 2002.

FIELD OF THE INVENTION

The present invention relates to the external fixation of bones during orthopedic surgical applications, such as the repair of bone fractures and the correction of bone defects. More particularly, the present invention relates to a method and apparatus which allow for gradual and controlled correction of bone deformities and malunions. The various applications of the present invention involve gradual angular, translational and rotational correction of bone deformities and malunions.

BACKGROUND OF THE INVENTION

In various orthopedic surgical procedures, it is necessary to secure two bone portions in a relatively fixed relationship to each other. For example, the need for establishing such a secured relationship is often a result of a fracture which has occurred to the bone. This secured relationship is also employed to correct deformities and malunions. To ensure that the bone can regenerate in the proper orientation and fuse the fracture, it is important that the bone portions be fixed and in the desired position during bone regeneration.

Various external fixation devices for the repair of traumatized bone are known. For example, commonly assigned U.S. Pat. No. 5,662,650 to Bailey et al. discloses an apparatus for the external fixation of large bones. The apparatus is illustrated to include a main body as well as a first and second bone screw clamps. The main body serves to allow the apparatus to axially rotate, thereby providing a proper longitudinal rotational location of the bone screws with respect to a bone. The first bone screw clamp is used to secure a first bone screw to the apparatus while permitting the first bone screw to be axially displaced from the main body. In a similar fashion, the second bone screw clamp functions to secure a second bone screw to the apparatus and to allow the second bone screw to be axially displaced with respect to the main body. U.S. Pat. No. 5,662,650 is incorporated by reference as if fully set forth herein.

In certain orthopedic surgical procedures, it is necessary to engage two bone portions in a fixed relationship and to angulate, rotate and/or translate the two bone portions relative to each other. The need for making such an adjustment is frequently the result of bone deformity. Such bone deformities may result from congenital defects including but not limited to Blount's Disease, Tibia Vara, and Hypophosphatemic Rickets. Adjustment of bone portions may also be required as a result of post-traumatic applications, such as the correction of bone malunions.

Other known devices are available for the correction of bone deformities and malunions. For example, commonly assigned U.S. Pat. No. 5,941,879 discloses an external fixator for adjustably securing a first bone portion in a position relative to a second bone portion. The fixator includes a first clamping assembly for receiving a first bone screw connected to the first bone portion and a second clamping assembly for receiving a second bone screw connected to the second bone portion. The first and second clamping assemblies are interconnected by a connection member. The external fixator also includes a drive unit for controlling angular adjustment of the second clamping assembly relative to the first clamping assembly.

While the fixators specifically for correcting bone deformities and malunions of the type described above may have proven acceptable for certain applications, such fixators are nevertheless susceptible to improvements that may enhance the performance of the fixator for particular applications.

SUMMARY OF THE INVENTION

In general, the present invention relates to the external fixation of bones. More specifically, the present invention relates to an external fixator which is operable to adjustably secure a first bone portion in a particular position with respect to a second bone portion.

An advantage of the present invention is the provision of a method and apparatus for the external fixation of bone which allows the rate of angular, rotational and/or translational correction of bone deformities and malunions to be easily and more accurately controlled.

In one particular form, the present invention provides a frame assembly for an external fixation device. The frame assembly includes a first arc segment and a second arc segment. The first arc segment is for interconnection to a first bone portion. The second arc segment is for interconnection to a second bone portion. The first arc segment is coupled to the second arc segment for controlled relative rotation.

In another particular form, the present invention provides an articulating module for an external fixation device. The articulating module includes a central member, a first pivot segment and a second pivot segment. The first pivot segment is coupled to the central member for driven rotation about a first pivot axis. The second pivot segment is coupled to the central member for driven rotation about a second pivot axis. The second pivot axis is substantially parallel to the first pivot axis.

In yet another particular form, the present invention provides a method of correcting a rotational deformity or malunion of a bone having a longitudinal axis. The method includes the step of providing an external fixation device including a frame assembly with a first arc segment coupled to a second arc segment. The method additionally includes the steps of interconnecting the first arc segment to a first bone portion and interconnecting the second arc segment to a second bone portion. The method further includes the step of rotating the first arc segment relative to the second arc segment to correct the rotational deformity or malunion of the bone.

Additional advantages and features of the present invention will become apparent from the following description and appended claims, taken in conjunction with the accompanying drawings.

BRIEF DESCRIPTION OF THE DRAWINGS

The present invention will become more fully understood from the detailed description and the accompanying drawings, wherein.

DETAILED DESCRIPTION OF THE PREFERRED EMBODIMENT

Figure 1:
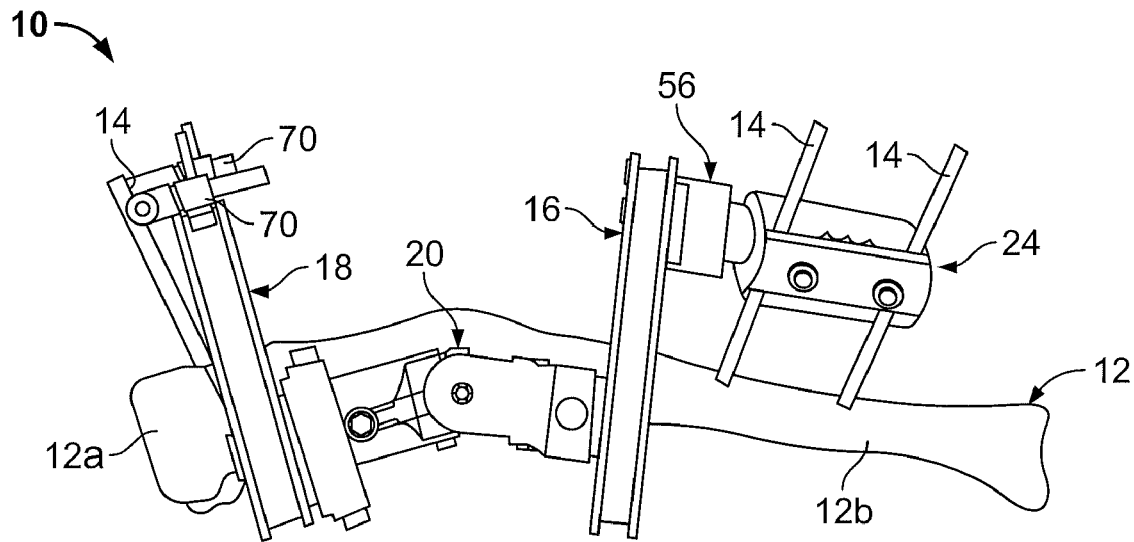
FIG. 1 is an environmental view of an apparatus for the external fixation and correction of bone according to the teachings of a preferred embodiment of the present invention, the apparatus shown operatively associated with a human tibia.
Figure 1A:
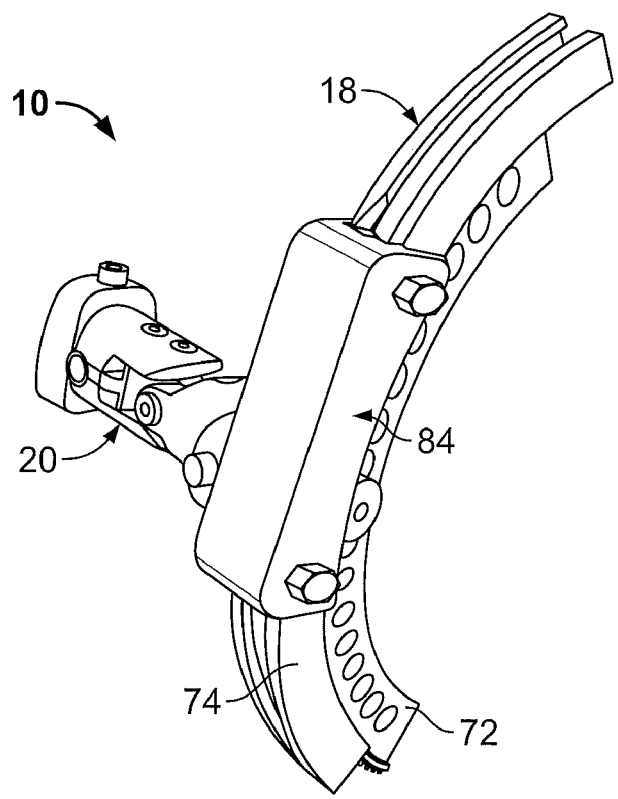
FIG. 1A is a perspective view of a portion of the apparatus according to the teachings of the preferred embodiment of the present invention.

The following description of the preferred embodiment(s) is merely exemplary in nature and is in no way intended to limit the invention, its application, or uses.

With general reference to FIGS. 1 through 17 of the drawings, an apparatus for the external fixation and correction of a bone constructed in accordance with the teachings of a preferred embodiment of the present invention is illustrated and generally identified at reference character 10. With particular reference to the environmental view of FIG. 1, the apparatus 10 is shown connected to a bone 12 through a plurality of bone screws 14 which serve to secure a first bone portion 12a relative to a second bone portion 12b.

In the exemplary application illustrated, the first and second bone portions 12a and 12b secured by the apparatus 10 are of a single bone 12. The bone 12 shown in the drawings represents a human tibia. It is to be understood, however, that the apparatus 10 may be operatively attached to a variety of other types of bones and used to correct bone deformities, correct malunions, or repair fractures. As will become apparent below, by securing the first and second bone portions 12a and 12b with the apparatus 10 of the present invention, the orientation of the first portion 12a relative to the second portion 12b may be angularly, rotationally, and translationally adjusted.

In the particular construct shown, the apparatus 10 is illustrated to generally include first and second frame assemblies 16 and 18 interconnected by an articulating module or adjustable module 20. The particular construct shown is further illustrated to include a bone screw clamping assembly 24. The second frame assembly is secured to the first bone portion 12a. The bone screw clamping assembly 24 is secured to the second bone portion 12b. The bone screw clamping assembly 24 is coupled to the first frame assembly 16. The first and second frame assemblies 16 and 18 are adjustably interconnected by the module 20.

As will become apparent to those of ordinary skill in the art, the teachings of the present invention may be employed in many different constructs for external fixation depending on the particular surgical application and further depending on surgeon preferences. The construct shown in the drawings will be understood to be merely exemplary. The various components of the apparatus 10 of the present invention may be alternatively utilized in different constructs involving some or all of the illustrated components. Additionally, the various components of the present invention may be used in connection with other components, some of which are commercially available from the assignee of the subject application under the registered trademark DynaFix®.

Figure 2:
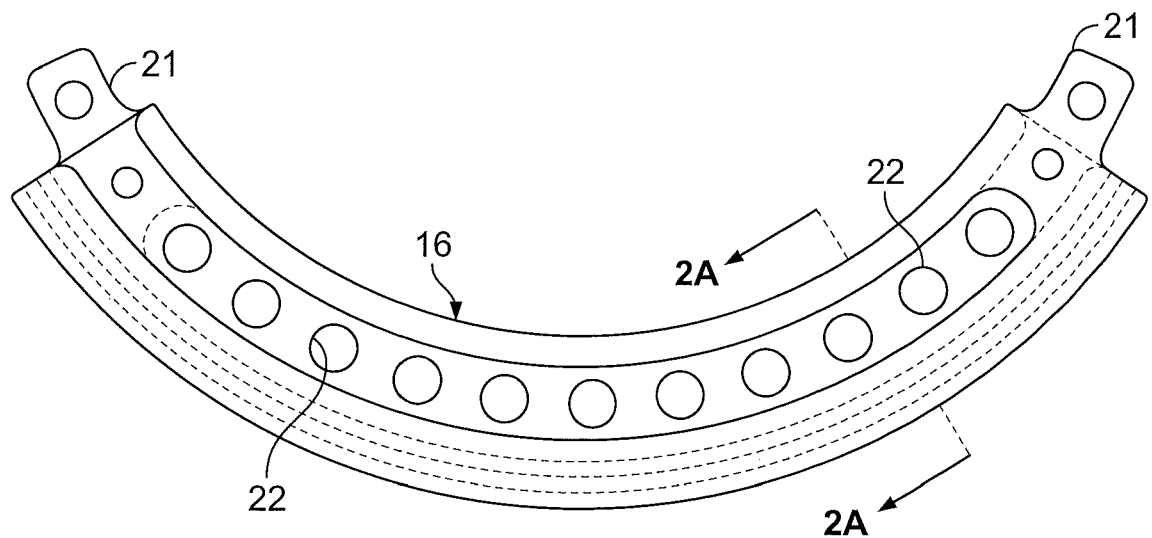
FIG. 2 is a top view of a first frame assembly of the external fixation and correction of bone according to the teachings of the preferred embodiment of the present invention.
Figure 2A:
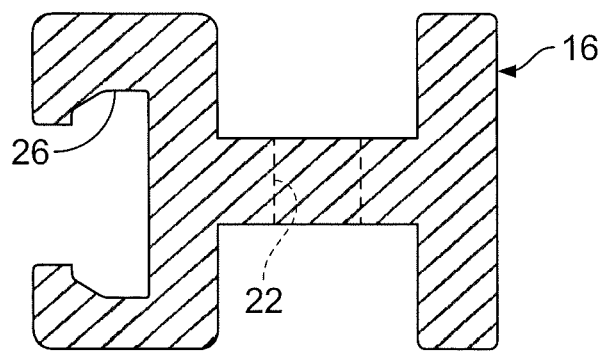
FIG. 2A is a cross-sectional view taken along the line 2A-2A of FIG. 2.
Figure 3:
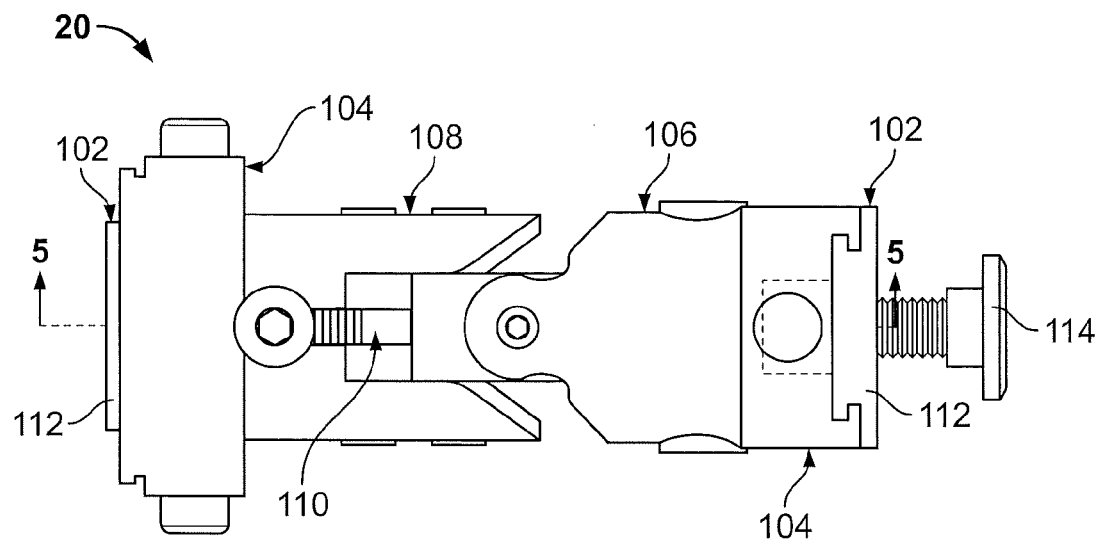
FIG. 3 is a side view of an articulating module of the apparatus according to the teachings of the preferred embodiment of the present invention.
Figure 4:
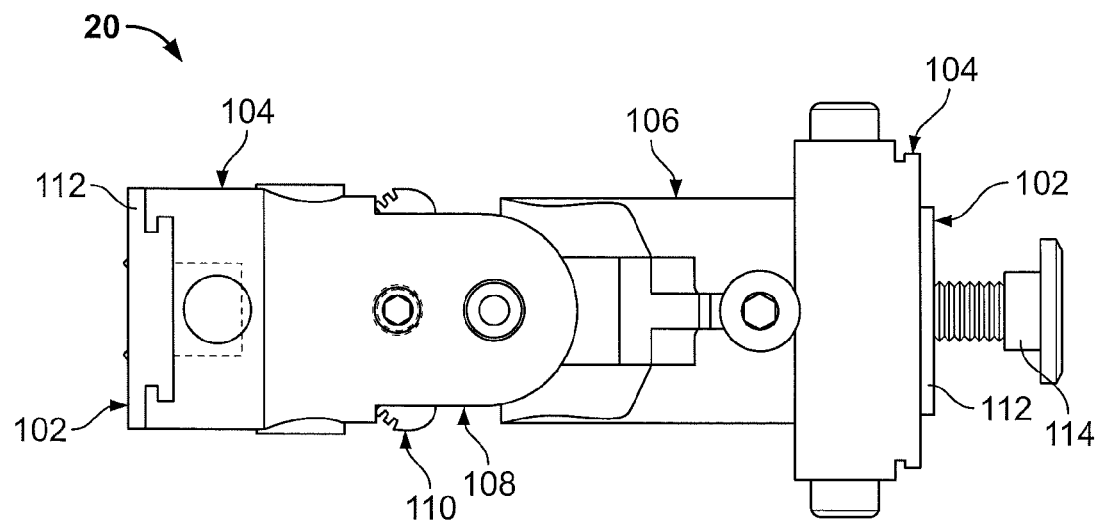
FIG. 4 is another side view of the articulating module of the apparatus according to the teachings of the preferred embodiment of the present invention.

The first frame assembly 16 defines an arc segment. In the embodiment illustrated, the first frame assembly 16 is shown to only partially circumscribe the bone 12. As shown most clearly in FIGS. 2 and 2A, the first frame assembly 16 defines approximately one-third of a complete circle. Alternatively, the first frame assembly 16 can be configured to define more or define less of an incomplete circle or configured as a complete ring to fully circumscribe the bone 12. The first frame assembly 16 is formed to include tabs 21 to facilitate attachment to additional segments (not shown). This arrangement and manner of attachment is more fully described in commonly assigned U.S. Pat. No. 5,997,537 which is hereby incorporated by reference as if fully set forth herein.

The first frame assembly 16 is formed to include a plurality of apertures 22 to facilitate attachment of the module 20 in a manner to be more fully addressed below. The first frame assembly 16 is further shown to define a groove 26 in an outer peripheral face to facilitate attachment of clamping elements. In the application illustrated, no clamping elements are employed for directly connecting the first frame assembly 16 to the bone 12.

Figure 11:
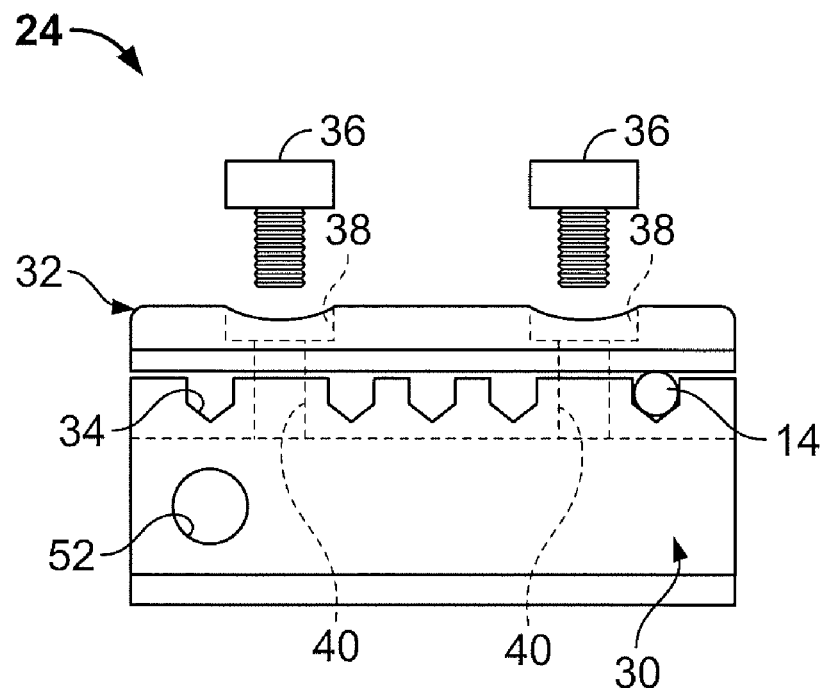
FIG. 11 is a side view of a bone screw clamping assembly of the apparatus according to the teachings of the preferred embodiment of the present invention.
Figure 11A:
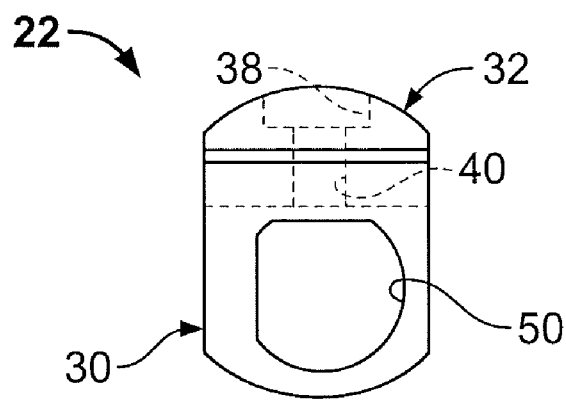
FIG. 11A is an end view of the bone clamping assembly of FIG. 11.
Figure 12:
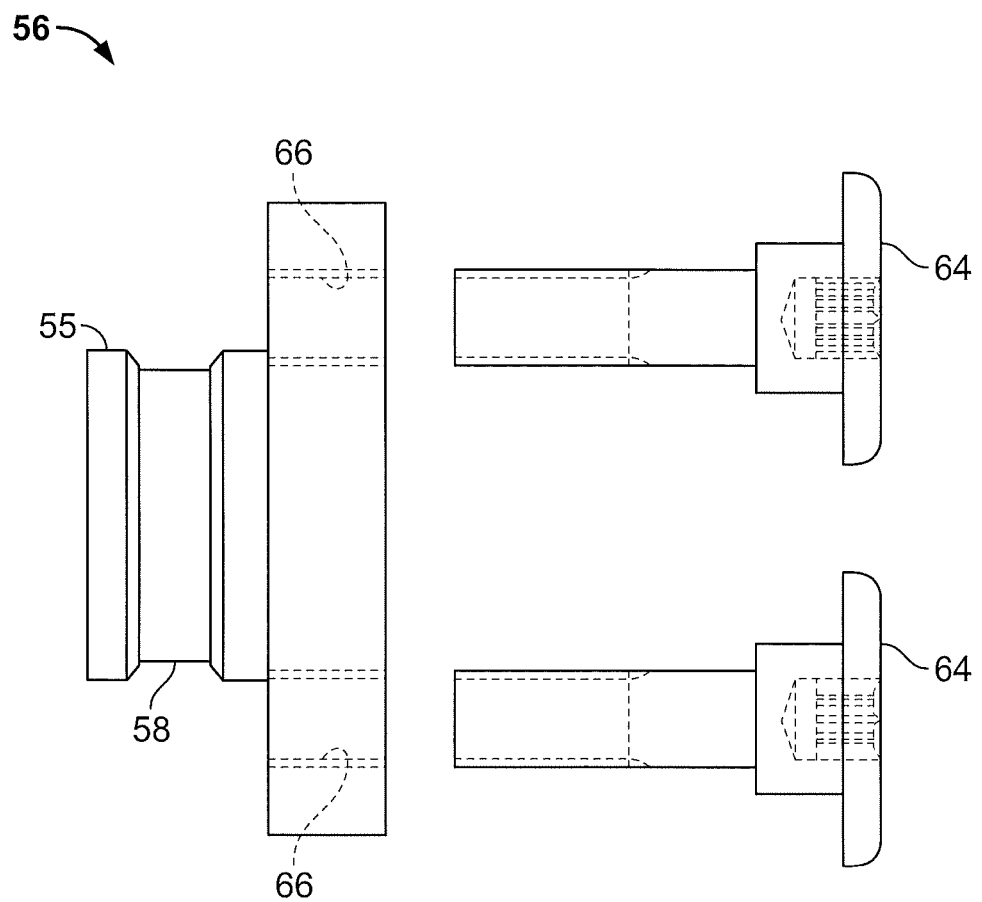
FIG. 12 is a partially exploded side view of a mounting member for connecting the bone screw clamping assembly with a first frame assembly of the apparatus according to the teachings of the preferred embodiment of the present invention.

With particular reference to FIGS. 11, 11A and 12, the bone screw clamping assembly 24 is shown to include a main body having a base portion 30 and a cover portion 32. The base portion 30 serves to receive a bone screw 14 in one of a plurality of grooves 34. The cover portion 32 serves to secure the bone screw 14 within the groove 34.

The cover portion 32 of the bone screw clamping assembly 24 is secured to the base portion 30 by two screws 36. To accommodate these screws 36, the cover portion 32 of the bone screw clamping assembly 24 includes two apertures 38 which mate with corresponding apertures 40 in the base portion 30 of the bone screw clamping assembly 24. Accordingly, upon secured threaded engagement of the screws 36 within the apertures 38 and 40, the cover portion 32 of the bone screw clamping assembly 24 may be secured to the base portion 30 of the bone screw clamping assembly 24.

Figure 13:
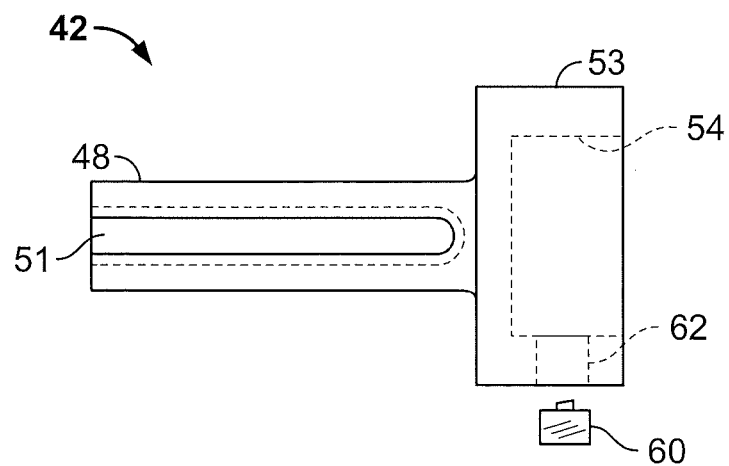
FIG. 13 is a side view of a rail member of the apparatus according to the teachings of the preferred embodiment of the present invention.
Figure 14:
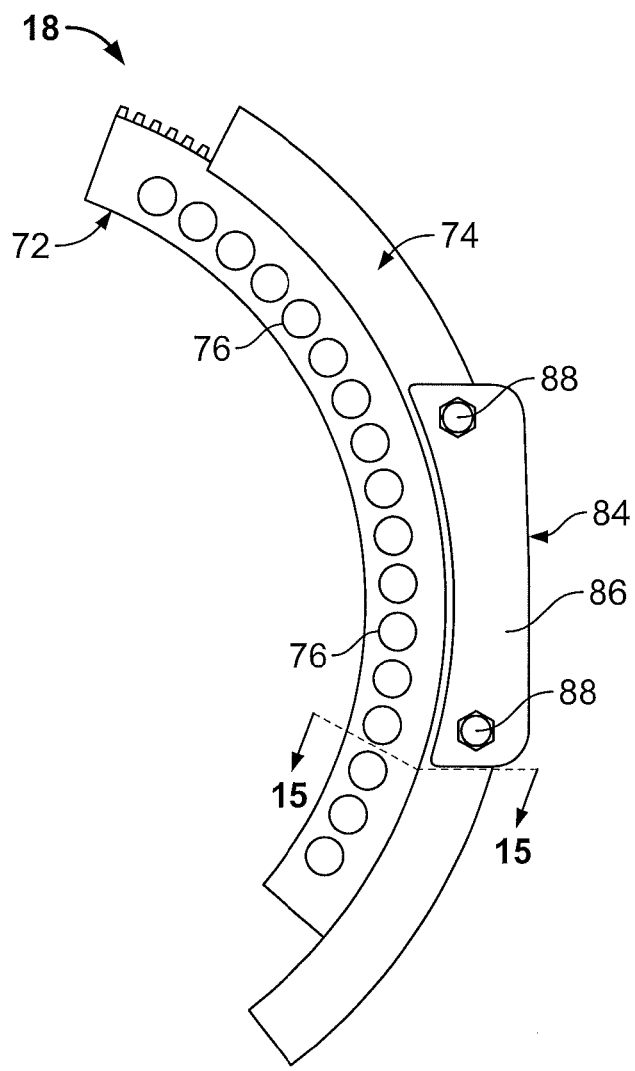
FIG. 14 is an end view of a second frame assembly of the apparatus according to the teachings of the preferred embodiment of the present invention.

With additional reference to FIG. 13, to provide for translation of the bone screw clamping assembly 24 relative to the first frame assembly 16, the bone screw clamping assembly 24 further includes a rail member 42. The rail member 42 preferably includes a D-shaped extension 48 which is able to be received in a D-shaped bore 50 of the bone screw clamping assembly 24. The D-shaped extension 48 includes an elongated slot 51 for receiving a set screw (not particularly shown) that extends through a threaded aperture 52 provided in the base portion 30. Because of the cross-sectional shape of the D-shaped extension 48, the base portion 30 of the bone screw clamping assembly 24 is able to slide on the extension 48 of the rail member 42. However, the base portion 30 is unable to rotate with respect to the D-shaped extension 48.

The rail member 42 has a generally circular end 53 defining a cylindrical aperture 54. The cylindrical aperture 54 receives a cylindrical portion 55 of a mounting member 56 (shown specifically in FIG. 12). The cylindrical portion 55 defines a reduced diameter groove 58 that receives a set screw 60 extending through an aperture 62 of the end 53.

A pair of threaded fasteners 64 extend through apertures 22 of the first frame assembly 16 and engage threaded apertures 66 of the mounting member 56. Prior to complete tightening of the set screw 60, the rail member 42 and thereby the clamp 24 are able to rotate about an axis parallel to the bone segment 12b.

With particular reference now to FIGS. 1 and 14 through 17, the second frame assembly 18 of the apparatus 10 constructed in accordance with the teachings of a preferred embodiment of the present invention will be further described. It will become apparent to those skilled in the art that the second frame assembly is specifically intended for the treatment of rotational deformities of bone. In other applications, it may be desirable to alternative use a frame assembly substantially identical to the first frame assembly 16 in place of the second frame assembly 18.

In the environmental view of FIG. 1, the second frame assembly 18 is shown operatively associated with a plurality of clamp members 70 and associated bone screws 14 for securing the second frame assembly 18 to the bone 12. The clamps 70 shown in FIG. 1 of the drawings engage an outer peripheral groove (similar in geometry to the groove 26 of the first frame assembly 16) of the second frame assembly 18 and illustrate one particular manner for attachment of the second frame assembly 18 to the bone 12. It will be understood by those skilled in the art that the particular manner of attachment of the second frame assembly 18 to the bone 12 is beyond the scope of the present invention and may be accomplished in any well known manner. One suitable manner of attachment is shown and described in commonly assigned U.S. Pat. No. 5,997,537.

The second frame assembly 18 of the preferred embodiment of the present invention is generally illustrated to include a first arc segment or member 72 and a second arc segment or member 74. The first and second arc segments 72 and 74 are coupled to one another for relative rotation. In the embodiment illustrated, the first and second arc segments 72 and 74 are concentrically arranged and the first arc segment 72 is illustrated as an inner arc segment. Similarly in this regard, the second arc segment 74 is illustrated as an outer arc segment.

As with the first frame assembly 16, the first arc member 72 of the second frame assembly 18 is formed to include a plurality of apertures 76 to facilitate connection to the module 20.

Further similar to the first frame assembly 16, the first and second arc segments 72 and 74 extend through approximately one-third of a complete circle. Alternatively, the first and second arc segments can be configured to define more or less of an incomplete circle or configured as a complete ring to fully circumscribe the bone 12.

Figure 15:
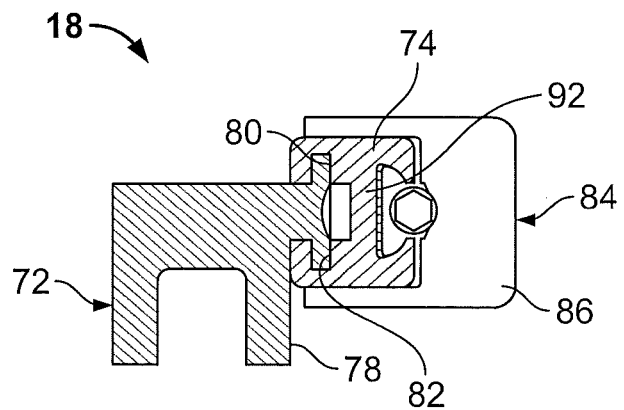
FIG. 15 is a cross-sectional view taken along the line 15-15 of FIG. 14.

As particularly shown in the cross-sectional view of FIG. 15, the first arc segment 72 has a main portion 78 having a downwardly opening U-shape. A upper horizontal segment connects two downwardly extending legs and defines the apertures 76. The first arc segment 72 further has a generally T-shaped extension 80 outwardly extending from the main portion 78. The T-shaped extension 80 is slidably received within a cooperative recess 82 of the second arc segment 72.

Figure 16:
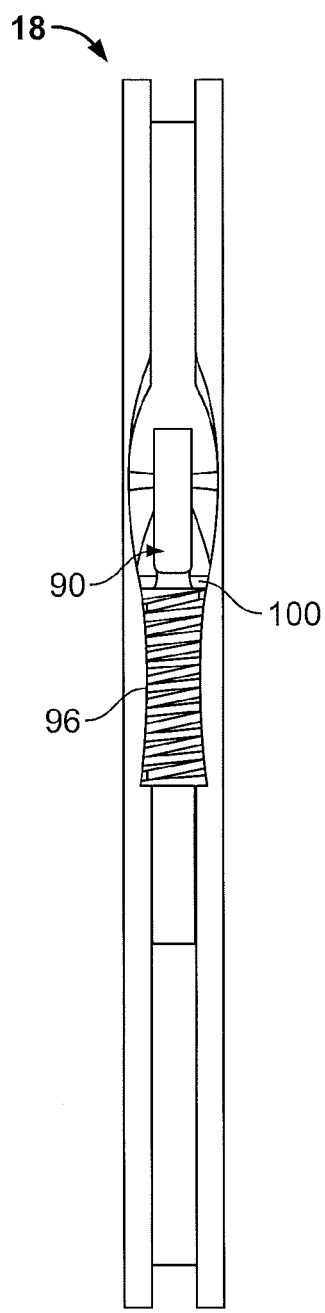
FIG. 16 is a side view of the second arc segment of the apparatus according to the teachings of the preferred embodiment of the present invention.
Figure 16A:
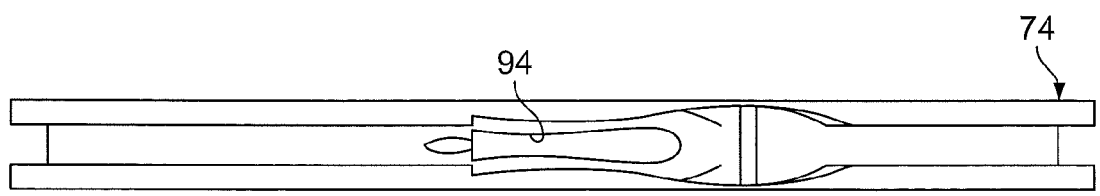
FIG. 16A is a side view of the second arc segment similar to FIG. 16, the worm gear removed for purposes of illustration.
Figure 17:
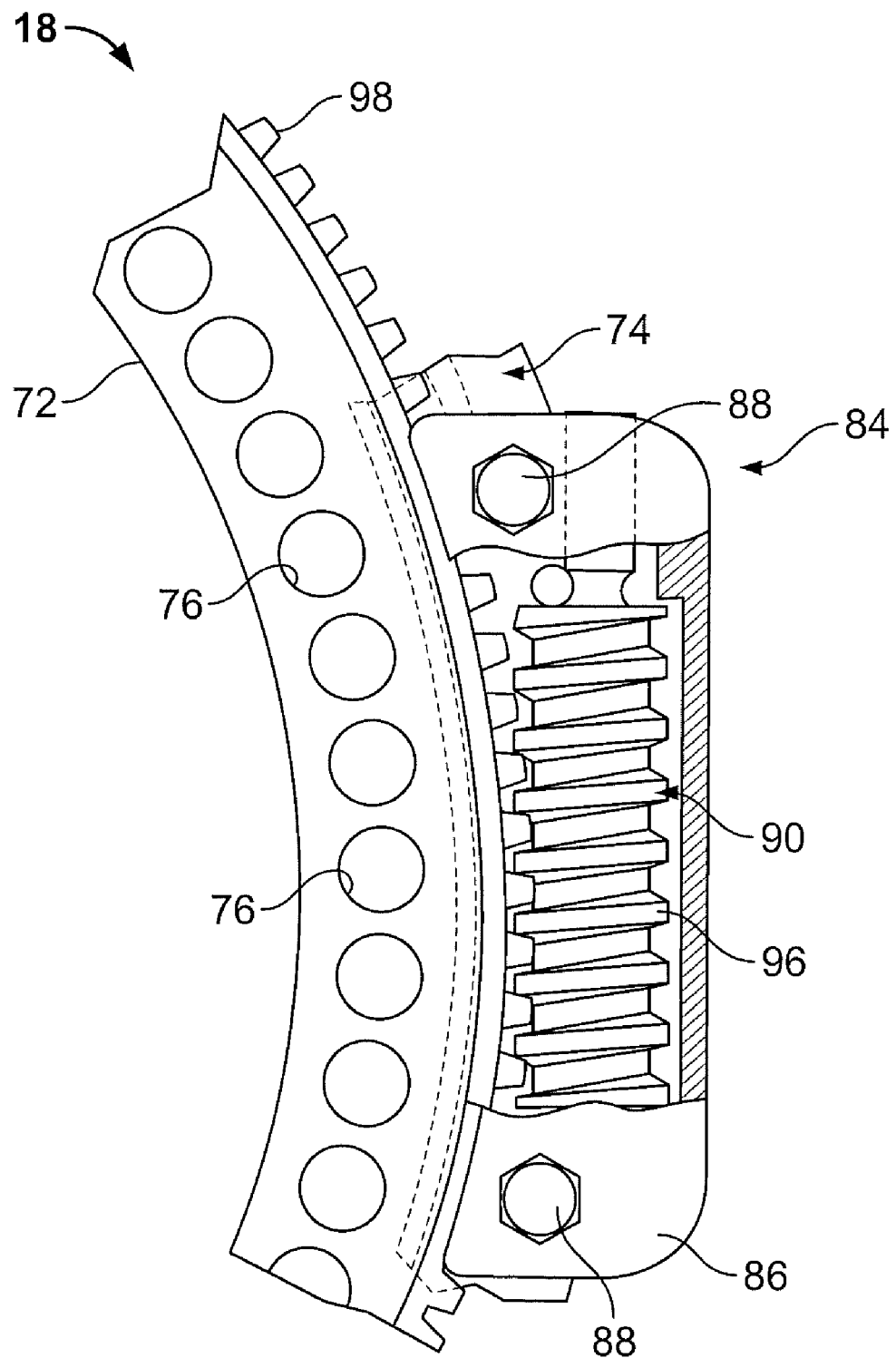
FIG. 17 is an enlarged end view of the second arc segment shown partially cutaway for purposes of illustration.

The second frame assembly 18 preferably includes a drive unit 84 for gradual and controlled rotation of the second arc segment 16 relative to the first arc segment 72. In the embodiment illustrated, the drive unit 84 includes a housing or cover 86 secured to the second arc segment 74 with a pair of fasteners 88. The drive unit 84 further includes a worm or worm gear 90. The worm gear 90 is rotatably carried by the second arc segment 74 and substantially disposed in the outer peripheral groove defined by the second arc segment 74. The second arc segment 74 is generally I-shaped. A vertically extending portion 92 of the second arc segment 74 defines an opening 94 (see FIG. 16A). The worm gear 90 includes a threaded portion 96. The threads of the threaded portion 96 partially extend through the opening 94 and a plurality of teeth 98 provided on an arcuate exterior portion of the first arc segment 72. In the embodiment illustrated, the plurality of teeth 98 are formed on an outer peripheral side of the T-shaped portion 80 and extend along the entire length of the first arc segment 72 to facilitate relative rotational movement between the first and second arc segments 72 and 74. A pin 100 (see FIG. 16) retains the worm gear 90 from translating relative to the second arc segment 74.

The common centers of curvature of the first and second arc segments 72 and 74 of the second frame assembly define a rotational axis about which the first bone portion 12a can be rotated relative to the second bone portion 12b. Significantly, this rotational axis can be postioned generally coincident with a long axis of the bone 12. Relative movement between the bone segments 12 and 12b is gear driven and thereby controlled and gradual.

With particular reference to FIGS. 1 and 1A and FIGS. 3 through 10, the module 20 of the preferred embodiment of the present invention will now be further described. The module 20 is generally illustrated to include a pair of mounting portions 102, a pair of translation segments 104, a first pivot segment 106, a second pivot segment 108 and a central member 110. The term "central" used to describe the central member 110 will be understood to reference the central location of the member 110 between the first and second pivot segments 106 and 108. The central member 110 need not be located centrally within the module 20.

A first of the mounting portion 102 functions to connect the module 20 with the first frame assembly 16. A second of the mounting portions 102 similarly functions to connect the module 20 with the second frame assembly 18. In the embodiment illustrated, the mounting portions 102 will be understood to be identical. The mounting portions 102 are illustrated to generally include a plate portion 112 and a single post or mounting member 114. The post 114 passes through one of the apertures of the respect frame assembly 16 or 18 and threadably engages an aperture 116 of the plate member 112. Insofar as interconnection of the module 20 with the frame assemblies 16 or 18 is made by a single post 114, relative rotation between the mounting members 102 and the remainder of the module 20 is not necessary. In this regard, the post 114 defines an axis about which the module 20 can rotate prior to complete tightening.

The translation segments 104 will be understood to be identical. As perhaps most clearly shown in the environmental view of FIG. 5, the translation segments 104 defines a groove 118 for slidably receiving a portion of the associated plate member 112. The translation segments 104 define a generally rectangular opening 120 and include a threaded worm 122. In the embodiment illustrated, the plate members 112 of the mounting portions 102 include a rectangular extension or carriage 124. These rectangular extensions 124 define the apertures 116 for receiving the posts 114. The worm 122 threadably engages an aperture 126 of the rectangular extension 124. The rectangular extension 124 is sized to be slidably received within the opening 120. Rotation of the worm 122 in a first direction operates to linearly translate the mounting member 102 relative to the associated translation segment 104 along an axis parallel to an axis defined by the worm 122.

The worms 122 provide two axes for relative translation between the first and second bone portions 12a and 12b. The worms 122 of the pair of translation segments 104 are preferably oriented generally perpendicular to one another. In this manner, the module 20 of the preferred embodiment of the present invention is able to provide gradual and controlled translation of the first bone portion 12a relative to the second bone portion 12b along two perpendicular axes.

The central member 110 is preferably unitarily constructed. As particularly shown in FIG. 6, the central member 110 includes a first end 130 having an arcuate flange 132. The flange 132 defines a first plurality of teeth 134. The central member 110 includes a second end 136 similarly including an arcuate flange 138 defining a second plurality of teeth 140. In the embodiment illustrated, the first plurality of teeth 134 are disposed in a plane substantially perpendicular to the second plurality of teeth 140.

The first pivot segment 106 downwardly extends from the upper translation segment 104. The first pivot segment 106 is illustrated to include a pair of spaced apart flanges 125 and a worm 126. The worm 126 threadably engages the first plurality of teeth 134 of the central member 110. A pin 142 (shown in FIG. 5) connects the flanges 125 with the plate central member 110 and defines a secondary pivot axis between the first and second pivot segments 106 and 108 of the module 20. The flanges 125 are cut-away to accommodate pivoting of the second pivot segment 108 about the pin 142. A set screw 143 is provided for selectively preventing relative rotation between the first pivot segement 106 and the central member 110.

The second pivot segment 108 upwardly extends from the lower one of the translation segments 104 and similar includes a pair of spaced apart flanges 144 and a worm 146. The worm 146 threadably engages the second plurality of teeth 140 of the central member 110. A pin 148 passes through the flanges 144 of the second pivot segment 108 and connects the flanges 144 with the central member 110. The pin 148 defines a primary pivot axis of the module 20. A set screw 149 is provided for selectively preventing relative rotation between the second pivot segment 108 and the central member 110.

In use, if the primary pivot defined by the pin 148 is exactly aligned with a pivot point of a bone deformity, no further adjustment of the module 20 is required. However, if the pivot axis defined by the pin 148 is not aligned exactly with the pivot point of the deformity, an angular deformity in a perpendicular plane and a translational deformity will be observed. The module 20 is adapted to correct the angle in a plane perpendicular to the primary pivot axis. In addition, the module 20 is adapted to correct translational deformities that may also result if the primary pivot axis is not exactly aligned with the pivot point of the deformity.

The module 20 defines two (2) perpendicular axes (i.e., along the pins 142 and 148) about which the bone portions 12a and 12b may be angulated relative to one another. This relative angulation is gear driven and gradual. Additionally, the module 20 includes two perpendicular translation axes (i.e., coincident with the worms 122 and 146). Again, this translation is gear driven and gradual. Furthermore, rotational axes are defined at the interconnections between the module 20 and the frame assemblies 16 and 18 (i.e., along the axis of the posts 114).

The description of the invention is merely exemplary in nature and, thus, variations that do not depart from the gist of the invention are intended to be within the scope of the invention. Such variations are not to be regarded as a departure from the spirit and scope of the invention.

In another particular form, the present invention provides an articulating module for an external fixation device. The articulating module includes a central member, a first pivot segment and a second pivot segment. The first pivot segment is coupled to the central member for driven rotation about a first pivot axis. The second pivot segment is coupled to the central member for driven rotation about a second pivot axis. The second pivot axis is substantially perpendicular to the first pivot axis.

The common centers of curvature of the first and second arc segments 72 and 74 of the second frame assembly define a rotational axis about which the first bone portion 12a can be rotated relative to the second bone portion 12b. Significantly, this retational axis can be positioned generally coincident with a long axis of the bone 12. Relative movement between the bone segments 12 and 12b is gear driven and thereby controlled and gradual.

The translation segments 104 will be understood to be identical. As perhaps most clearly shown in the environmental view of FIG. 5, the translation segments 104 defines a groove 118 for slidably receiving a portion of the associated plate member 112. The translation segments 104 define a generally rectangular opening 120 and include a threaded worm 122. In the embodiment illustrated, the plate members 112 of the mounting portions 102 include a rectangular extension or carriage 124. These rectangular extensions 124 define the apertures 116 for receiving the posts 114. The worm 122 threadably engages an aperture 129 of the rectangular extension 124. The rectangular extension 124 is sized to be slidably received within the opening 120. Rotation of the worm 122 in a first drection operates to linearly translate the mounting member 102 relative to the associated translation segment 104 along an axis parallel to an axis defined by the worm 122.

The module 20 defines two (2) perpendicular axes (i.e., along the pins 142 and 148) about which the bone portions 12a and 12b may be angulated relative to one another. This relative angulation is gear driven and gradual. Additionally, the module 20 includes two perpendicular translation axes (i.e., coincident with the two worms 122 shown in FIG. 5). Again, this translation is gear driven and gradual. Furthermore, rotational axes are defined at the interconnections between the module 20 and the frame assemblies 16 and 18 (i.e., along the axis of the posts 114).

The first pivot segment 106 downwardly extends from the upper translation segment 104. The first pivot segment 106 is illustrated to include a pair of spaced apart flanges 125 and a worm 126. The worm 126 threadably engages the first plurality of teeth 134 of the central member 110. A pin 142 (shown in FIG. 5) connects the flanges 125 with the plate central member 110 and defines a secondary pivot axis "B" (shown in FIG. 6) between the first and second pivot segments 106 and 108 of the module 20. The flanges 125 are cut-away to accommodate pivoting of the second pivot segment 108 about the pin 142. A set screw 143 is provided for selectively preventing relative rotation between the first pivot segment 106 and the central member 110.

The second pivot segment 108 upwardly extends from the lower one of the translation segments 104 and similar includes a pair of spaced apart flanges 144 and a worm 146. The worm 146 threadably engages the second plurality of teeth 140 of the central member 110. A pin 148 passes through the flanges 144 of the second pivot segment 108 and connects the flanges 144 with the central member 110. The pin 148 defines a primary pivot axis "A" (shown in FIG. 6) of the module 20. A set screw 149 is provided for selectively preventing relative rotation between the second pivot segment 108 and the central member 110.

The invention claimed is:

1. An external bone fixation device comprising:
an orthopedic articulating module mountable on bone, the articulating module comprising:
a monolithic central member having first and second arcuate ends and a central portion extending along a longitudinal axis, the first arcuate end defining a first substantially planar flange having a first plurality of teeth, the first substantially planar flange having a first width measured on the first flange perpendicular to the longitudinal axis, the first width tapering from the first arcuate end towards the central portion, and the second arcuate end defining a second substantially planar flange having a second plurality of teeth, the second substantially planar flange having a second width measured on the second flange perpendicular to the longitudinal axis, the second width tapering from the second arcuate end towards the central portion wherein the first and second flanges are substantially perpendicular to one another;
a first pivot segment coupled to the central member for driven rotation about a first pivot axis, the first pivot segment including a first pair of spaced-apart flanges and a first elongated worm member meshingly engaging the first plurality of teeth;
a first pivot pin passing through the central member along the first pivot axis substantially perpendicular to the first substantially planar flange, the first pivot pin coupling the first pair of spaced-apart flanges to the central member;
a second pivot segment coupled to the central member for driven rotation about a second pivot axis, the second pivot axis being substantially perpendicular to the first pivot axis, the second pivot segment including a second pair of spaced-apart flanges and a second elongated worm member meshingly engaging the second plurality of the teeth, the second elongated worm member perpendicular to the first elongated worm member; and
a second pivot pin passing through the central member along the second pivot axis perpendicular to the second substantially planar flange, the second pivot pin coupling the second pair of spaced-apart flanges to the central member.

2. The external bone fixation device of claim 1, wherein the first and second arcuate ends extend along arcs subtending angles less than 180 degrees.

3. An external bone fixation device comprising:
first and second orthopedic mounting members mountable on bone; and
an articulating module coupled to the mounting members, the articulating module comprising:
a monolithic central member having first and second arcuate ends and a central portion extending along a longitudinal axis, the first arcuate end defining a first flange having a first plurality of teeth along an arc subtending an angle less than 180 degrees and the second arcuate end defining a second flange having a second plurality of teeth along an arc subtending an angle less than 180 degrees, wherein the first and second flanges are at opposite ends of the central portion and substantially perpendicular to one another, the first and second flanges having corresponding first and second widths measured on the first and second flanges perpendicular to the longitudinal axis, the first and second widths tapering from the first and second arcuate ends towards the central portion; and
first and second translation segments coupled to the central member, the first and second translation segments including corresponding first and second threaded worm members meshingly coupled to the first and second mounting members for controlled translation along first and second translation axes, the second translation axis being substantially perpendicular to the first translation axis and substantially perpendicular to the longitudinal axis of the central member.

4. The device of claim 3, further comprising first and second pivot segments respectively extending from the first and second translation segments, the first and second pivot segments pivotably coupled to the central member for controlled rotation about respective first and second pivot axes, wherein the first pivot axis is substantially perpendicular to the second pivot axis.

5. The device of claim 4, wherein the first and second pivot segments include corresponding first and second threaded worm members substantially perpendicular to one another and meshingly engaged with the central member for relative rotation about the corresponding first and second pivot axes.

6. An articulating module for an external bone fixation device, the articulating module comprising:
a monolithic central member having first and second arcuate ends along a longitudinal axis, the first arcuate end defining a first substantially planar flange having a first plurality of teeth and the second arcuate end defining a second substantially planar flange having a second plurality of teeth, wherein the first and second substantially planar flanges are substantially perpendicular to one another;
first and second pivot segments coupled to the central member for rotation about first and second pivot axes, the first and second pivot axes being substantially perpendicular to one another and to the longitudinal axis;
first and second worm members meshingly engaging the first and second pluralities of teeth respectively, the first and second worm members being substantially perpendicular to one another;

first and second mounting members mountable on bone; and first and second translation segments extending from the first and second pivot segments, the first and second translation segments including corresponding third and fourth threaded worm members meshingly engaged with the corresponding first and second mounting members for translation along first and second translation axes, the first and second translation axes being substantially perpendicular to one another and to the longitudinal axis of the central member.

* * * * *

UNITED STATES PATENT AND TRADEMARK OFFICE
CERTIFICATE OF CORRECTION

PATENT NO.      : 7,449,023 B2                                      Page 1 of 2
APPLICATION NO. : 10/619536
DATED           : November 11, 2008
INVENTOR(S)     : Stephen B. Walulik et al.

It is certified that error appears in the above-identified patent and that said Letters Patent is hereby corrected as shown below:

Column 1
Line 39, delete "a" before first.

Column 2
Line 39, "parallel" should be --perpendicular--.

Column 5
Line 46, "alternative" should be --alternatively--.

Column 6
Line 19, "A" should be --An--.

Column 6
Line 51, "postioned" should be --positioned--.

Column 7
Line 25, "126" should be --129--.

Column 7
Line 54, insert --"B" (shown in FIG. 6)-- after axis.

Column 7
Line 59, "segement" should be --segment--.

Column 7
Line 62, "similar" should be --similarly--.

Column 8
Line 1, insert --"A" (shown in FIG. 6)-- after axis.

Column 8
Line 21, insert --two-- after the.

Signed and Sealed this

Ninth Day of November, 2010

David J. Kappos
*Director of the United States Patent and Trademark Office*

Column 8
Line 21, delete "and 146" after 122.

Figure 5:
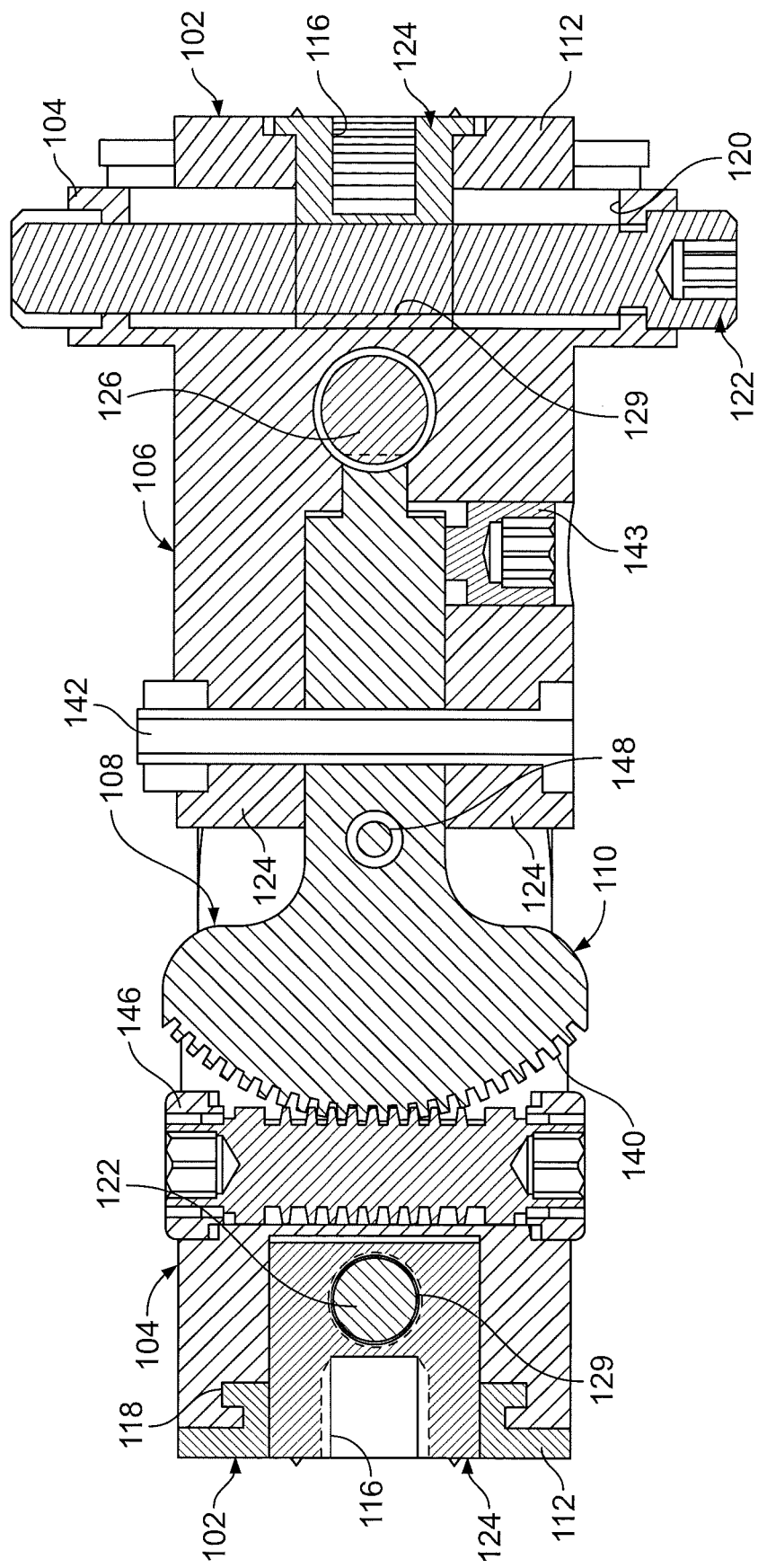
FIG. 5 is a cross-sectional view taken along the line 5-5 of FIG. 3.
Figure 6:
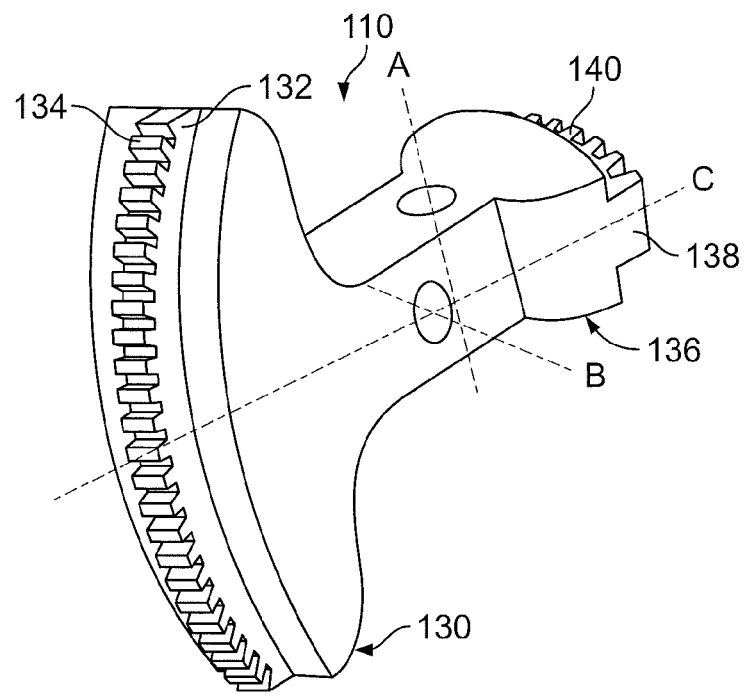
FIG. 6 is a perspective view of a central member of the articulating module of the apparatus according to the teachings of the preferred embodiment of the present invention.
Figure 7:
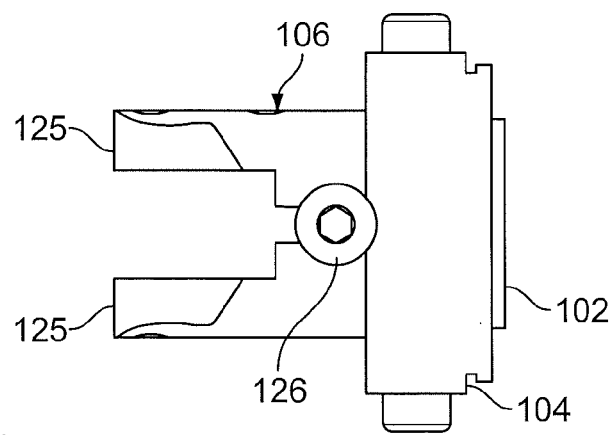
FIG. 7 is a side view of a first pivot segment and an associated translation module of the articulating module of the apparatus according to the teachings of the preferred embodiment of the present invention.
Figure 8:
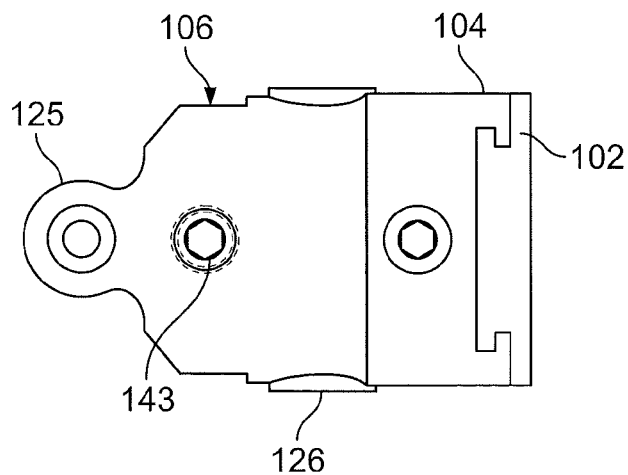
FIG. 8 is a top view of the first pivot segment and associated translation module of FIG. 7.
Figure 9:
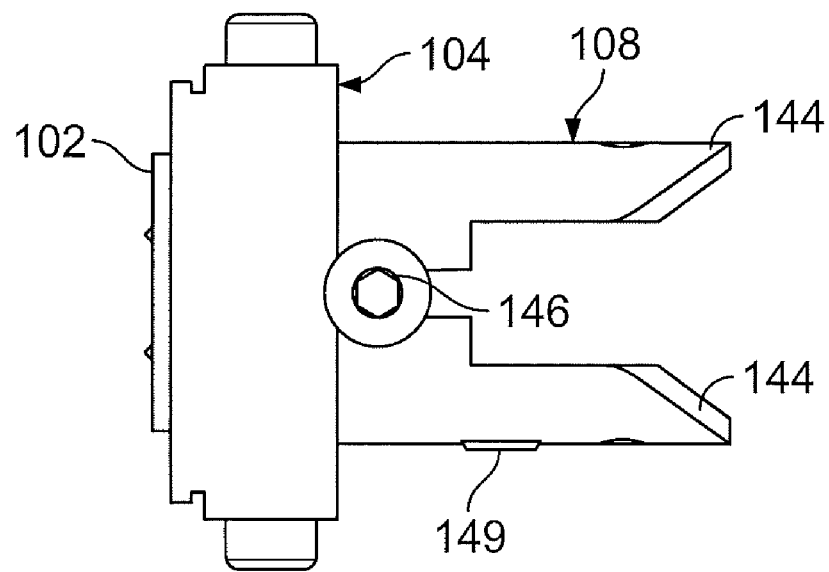
FIG. 9 is a side view of a second pivot segment and an associated translation module of the articulating module of the apparatus according to the teachings of the preferred embodiment of the present invention.
Figure 10:
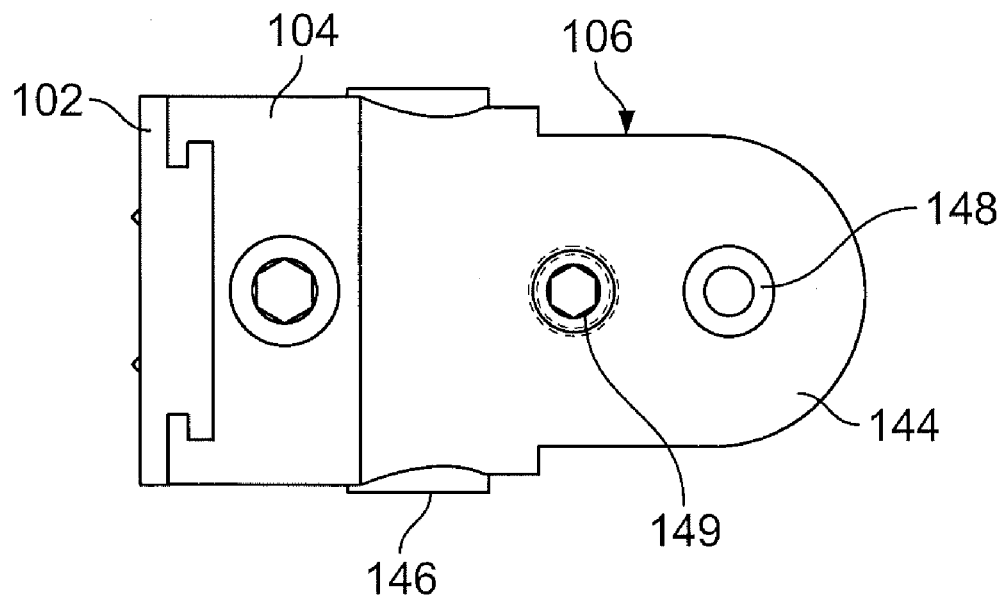
FIG. 10 is a top view of the second pivot segment and associated translation module of FIG. 9.

Column 8
Line 21, insert --shown in FIG. 5-- after 122.

Column 8
Line 31 through Column 9, Line 30: completely delete lines starting from 31 of column 8 to line 30 of column 9.